United States Patent
Grimes et al.

(10) Patent No.: US 6,630,130 B1
(45) Date of Patent: Oct. 7, 2003

(54) SUNLESS TANNING CREAM

(75) Inventors: Pearl Grimes, 340 S. Lorraine Blvd., Los Angeles, CA (US) 90020; Irwin Palefsky, Clifton, NJ (US); Ken Klein, Fairlawn, NJ (US)

(73) Assignee: Pearl Grimes, Los Angeles, CA (US)

( * ) Notice: Subject to any disclaimer, the term of this patent is extended or adjusted under 35 U.S.C. 154(b) by 125 days.

(21) Appl. No.: 09/906,184

(22) Filed: Jul. 16, 2001

(51) Int. Cl.[7] ............... A61K 7/42; A61K 31/12
(52) U.S. Cl. .................... 424/59; 514/675
(58) Field of Search .............. 424/59; 514/675

(56) References Cited

U.S. PATENT DOCUMENTS

| | | |
|---|---|---|
| 2,949,403 A | 8/1960 | Andreadis et al. |
| 4,708,865 A | 11/1987 | Turner |
| 4,985,443 A | 1/1991 | Montes |
| 5,318,774 A | 6/1994 | Alban et al. |
| 5,433,942 A | 7/1995 | Wood et al. |
| 5,662,890 A | 9/1997 | Punto et al. |
| 5,972,313 A | 10/1999 | Tuloup et al. |
| 5,972,314 A | 10/1999 | Crotty et al. |
| 6,143,723 A | 11/2000 | Ramaiah |
| 6,171,605 B1 | 1/2001 | Bevacqua et al. |
| 2003/0003065 A1 * | 1/2003 | Kalla et al. .......... 424/63 |

* cited by examiner

Primary Examiner—Shelley A. Dodson
(74) Attorney, Agent, or Firm—Pearne & Gordon LLP

(57) ABSTRACT

A sunless tanning formulation is provided to impart a cosmetic coloring effect to skin. The formulation is particularly useful to camouflage the effects of vitiligo. The formulation has both makeup coloring components for instant coloring effect, and dihydroxyacetone for a lasting coloring effect. The formulation is a water-in-oil emulsion with water being the inner phase and oil being the outer phase. A method of camouflaging depigmented splotches resulting from vitiligo using dihydroxyacetone is also provided.

36 Claims, No Drawings

SUNLESS TANNING CREAM

BACKGROUND OF THE INVENTION

The invention relates to a sunless tanning cream effective as a self tanning formulation and in camouflaging the effects of vitiligo on human skin.

Millions of people desire efficacious products to camouflage skin imperfections as well as the effects of leukodermic conditions such as vitiligo. In addition, many of the same people also want tanned skin. Despite the well documented negative effects of long-term exposure to ultraviolet light, global populations generally equate tanned skin with health and affluence. Present sunless tanning products have proven inadequate to serve the above needs of consumers, particularly African American consumers, due to inadequate match of skin tone and poor functional longevity.

It would be advantageous to provide a sunless tanning cream that effectively provides the appearance of tanned skin without having to go into the sun. It would be even more advantageous if such a cream would produce an immediate tanned appearance and last for an extended period of time.

Furthermore, it is desirable that such a sunless tanning cream, in addition to effectively tanning healthy skin of people in the general population, would also effectively camouflage the unsightly effects of vitiligo. Vitiligo is a chronic depigmentation disorder that causes unsightly white patches or splotches on the patient's skin. These splotches are caused by localized depigmentation at discrete sites over the skin surface. Vitiligo affects people of all ethnicities and races. However, its effects are particularly pronounced in African American patients due to the high contrast between their natural brown or black skin and the bright white splotches characteristic of vitiligo.

While the patient suffers no debilitating effects from vitiligo, it often can have a negative psychological impact, particularly in African Americans for the above reason. Consequently, a number of creams have been developed primarily comprised of a makeup base which do not medically treat the vitiligo, but are designed to mask its effects by camouflaging the depigmented splotches.

However, current makeup-based creams, e.g. Dermablend, Coverblend, and Dermacolor, suffer from a number of drawbacks in their application. Specifically, existing creams mask white splotches for only limited periods of time before washing or rubbing off. Consequently, such creams must be applied at least daily to provide any lasting benefit to the wearer. In addition, existing creams have an objectionable feel on the skin which is unpleasant to the touch. Existing creams also tend not to be well matched to the various skin tones of African American vitiligo patients.

Consequently, there is a need in the art for a sunless tanning cream that provides a lasting tanned appearance, and that successfully masks the effects of vitiligo for an extended period of time in a manner that cannot be washed or rubbed off. Preferably, such a cream would not be objectionable to the touch, and would be well matched to the skin tone of the wearer, particularly for African Americans.

SUMMARY OF THE INVENTION

A sunless tanning formulation is provided which comprises a non-makeup cosmetic and a coloring system. The coloring system comprises a makeup. The non-makeup cosmetic is effective to darken the epidermis via a chemical reaction. Also provided is a sunless tanning formulation that is effective to camouflage the effects of vitiligo when applied to skin. The formulation is a water-in-oil emulsion having an inner water phase and an outer oil phase, and comprises an effective amount of dihydroxyacetone, a coloring system comprising oil-soluble and water-soluble coloring agents, an emulsifying system effective to provide a water-in-oil emulsion, and a solvent system comprising silicone-based solvents.

A method of camouflaging the effects of vitiligo is also provided. The method comprises the step of applying an effective amount of DHA to a depigmented splotch on a patient's skin.

A method of providing the appearance of tanned skin is also provided. The method comprises step of applying a sunless tanning preparation to the skin, wherein the preparation has a makeup and dihydroxyacetone. The makeup provides an immediate coloring effect yielding the appearance of tanned skin, while the dihydroxyacetone undergoes a chemical reaction with the epidermis to provide a lasting appearance of tanned skin after the makeup has washed away.

DETAILED DESCRIPTION OF THE PREFERRED EMBODIMENTS OF THE INVENTION

As used herein, when a range such as 5–25 or between 5 and 25 is given, this means preferably at least 5 and, separately and independently, preferably not more than 25. Also as used herein, "cosmetic" means any component or substance that improves the general appearance of skin, thus yielding a "cosmetic effect." A "cosmetic effect" means the effect of improved skin appearance through application or use of a "cosmetic."

As used herein, the term "makeup" means a cosmetic in the form of a pigment, dye, or other colored material, whose sole function is to create the appearance of color when applied to the skin, the apparent color being that of the "makeup" itself. As used herein, "non-makeup cosmetic" means a cosmetic that is not in the form of a pigment, dye, or other similar colored material that creates the appearance of color when applied to the skin, the apparent color being that of the pigment, dye or other similar colored material.

The invented formulation is provided preferably in the form of a cream, less preferably as a gel, spray or aerosol, less preferably in some other known form applicable to the skin. The formulation is effective in camouflaging the unsightly white splotches characteristic of vitiligo, particularly in African American patients. The formulation is dispensed preferably from a soft tube, less preferably from a jar, bottle, pump, can, spray can or spray bottle, less preferably from some other known container.

The invented formulation has the preferred compositions of components shown in table 1 below. It should be noted that table 1 defines four separate preferred embodiments of the invention. The four preferred embodiments differ in the color of their respective cosmetic effects (light brown, brown, dark brown, and honey), with each of the preferred embodiments differing primarily in the most preferred concentrations of the coloring system components. The four preferred formulations are substantially similar in other respects. In table 1, any preferred or less preferred weight percent or weight percent range of any component can be combined with any preferred or less preferred weight percent or weight percent range of any of the other components; it is not required or necessary that all or any of the weight percents or weight percent ranges come from the same column. The column labeled "Phase" refers to the preferred order and method of mixing the components, and is explained in detail below. Unless otherwise specified, all concentrations are weight percents.

5–6, most preferably about 5.5. Compatible emulsifiers also preferably have no functional amino groups, particularly no primary amino groups. Preferably, the emulsifying system comprises PEG-30 dipolyhydroxystearate, sorbitan isostearate, dimethicone copolyol beeswax, and decyl

TABLE 1

Colored formulation

| Phase | Component System | Ingredient | Trade Name | Preferred (Honey) | Preferred (Light Brown) | Preferred (Brown) | Preferred (Dark Brown) | Less Preferred | Less Preferred |
|---|---|---|---|---|---|---|---|---|---|
| A | Solvent | Cyclopentasiloxane/ Dimethicone Copolyol | SF 1528 | 8 | 8 | 8 | 8 | 4–15 | 0.5–30 |
| A | Solvent | Cyclometicone | DC-245 | 5 | 5 | 5 | 5 | 1–15 | 0.5–30 |
| A | Solvent | Diisodecyl Adipate | Trivent DIDA | 5 | 5 | 5 | 5 | 1–15 | 0.5–30 |
| A | Solvent | Dimethicone | DC-200 | 1 | 1 | 1 | 1 | 0.7–10 | 0.5–30 |
| A | Emulsifying | Dimethicone Copolyol Beeswax | Siliconyl Beeswax | 0.4 | 0.4 | 0.4 | 0.4 | 0.2–5 | 0.1–10 |
| A | Solvent | Hydrogenated Castor Oil | Castor Wax MP70 | 1 | 1 | 1 | 1 | 0.2–4 | 0.1–10 |
| A | Emulsifying | PEG-30 Dipolyhydroxystearate | Arlacel P-135 | 0.5 | 0.5 | 0.5 | 0.5 | 0.2–4 | 0.1–10 |
| A | Emulsifying | Sorbitan Isostearate | — | 0.3 | 0.3 | 0.3 | 0.3 | 0.2–4 | 0.1–10 |
| A | Coloring | D&C Violet #2 (1% in mineral oil) | — | 0.4 | 0.49 | 0.5 | 0.75 | 0.1–3 | 0.01–5 |
| A | Coloring | D&C Green #6 (1% in mineral oil) | — | 0.2 | 0.26 | 0.3 | 0.45 | 0.1–3 | 0.01–5 |
| A | Coloring | D&C Red #17 (1% in mineral oil) | — | 0.82 | 0.97 | 1 | 1.5 | 0.1–3.5 | 0.01–5 |
| B | — | Deionized Water | — | 61.77 | 58.21 | 50.9 | 39 | 10–65 | 5–70 |
| B | Coloring | Melanin (10% solution) | — | 0.01 | 0.12 | 1 | 5 | 0.005–6 | 0.001–8 |
| B | Coloring | Propylene Glycol/ Indigofera Tintoria Root Extract | Actiphyte Black Henna BG50P | 0.5 | 0.5 | 0.5 | 1 | 0.1–4 | 0.01–15 |
| B | Coloring | Junglens Regia Extract | Walnut Leaf Extract #336 | 2 | 1.99 | 1.5 | 3 | 1–6 | 0.01–15 |
| B | Coloring | FD&C Red #33 (1% in water) | — | 0.2 | 0.5 | 1 | 5 | 0.1–8 | 0.01–15 |
| B | Coloring | FD&C Yellow #5 (1% in water) | — | 3 | 3.58 | 7 | 7 | 0.1–9 | 0.01–15 |
| B | Coloring | FD&C Blue #1 (0.1% in water) | — | 0.8 | 1.04 | 2 | 2 | 0.1–4 | 0.01–15 |
| B | Emulsifying | Decyl Glucoside | Plantaren 2000 | 0.1 | 0.1 | 0.1 | 0.1 | 0.05–3 | 0.01–10 |
| B | Solvent | Sodium Chloride | — | 1 | 1 | 1 | 1 | 0.1–3 | 0.01–10 |
| B | Antimicrobial | Propylene Glycol/ Urea/Propyl Paraben | Germaben II | 1 | 1 | 1 | 1 | 0.1–3 | 0.1–5 |
| C | — | Dihydroxyacetone | — | 2 | 4.04 | 6 | 7 | 1.4–8.5 | 1.0–10 |
| C | — | Deionized Water | — | 5 | 5 | 5 | 5 | 5.0–35 | 5.0–70 |

The formulation contains a non-makeup cosmetic, preferably dihydroxyacetone (DHA), in an amount effective to darken the epidermis via a chemical reaction as is known in the dermatologic art, thus yielding a true cosmetic effect. Less preferably, other known non-makeup cosmetics which darken the epidermis via a chemical reaction can be used. The formulation also contains a makeup, preferably a combination of multiple makeups, collectively referred to herein as the coloring system. Preferably, the invented formulation further contains a solvent system and an emulsifying system.

The invented formulation preferably is provided as a water in oil emulsion, with the water phase being the internal phase and the oil phase being the external phase. The emulsifying system is effective to accomplish this purpose. The emulsifying system preferably comprises emulsifiers, preferably PEG esters, that are compatible with DHA. Compatible emulsifiers are not prone to hydrolysis and preferably have a low pH, preferably 4–7, more preferably glucoside, less preferably PEG esters of triglycerides and/or low ethoxylate nonionic surfactants. Less preferably, the emulsifying system comprises ethoxylated alcohols and/or glycerol esters.

The solvent system preferably comprises at least one silicone-based solvent, most preferably the following silicone-based solvents: cyclopentasiloxane with dimethicone copolyol, cyclometicone, and dimethicone. Preferably, the solvent system also contains an emollient ester such as diisodecyl adipate in a quantity effective to abate the objectionable feel and improve the spreadability of the silicone-based solvents over the skin. Diisodecyl adipate also aids solubilization of oil-soluble makeup components in the silicone phase. Other suitable emollient esters include isopropyl myristate, decyl oleate, and other emollient esters known in the art which are effective to improve spreadability and feel. Such a preferred silicone-based solvent system has been shown to provide an outer emulsion phase that spreads easily and evenly over the skin, has little or no objectionable feel, and effectively solvates oil-based makeup components for good color longevity. Less preferably, other silicone-based solvents can be used. Even less preferably, other non-silicone based solvents capable of solvating oil-soluble color components may be used in the oil phase. Silicone-based solvents are generally preferred because they provide a formulation that has high wearability, and is aesthetic in appearance compared to other non-silicone based solvents.

The coloring system preferably contains both water-and oil-soluble makeup components. Preferably, the water-soluble makeup components comprise at least one or a mixture of D&C and/or FD&C coloring agents as are known in the art. Preferably, the oil-soluble makeup components comprise at least one or a mixture of natural pigments, synthetic pigments, plant extracts, fruit extracts, vegetable extracts, and/or other oil-soluble makeup components as known in the art.

Preferably, the invented formulation also contains sodium chloride as an emulsion stabilizer as well known in the art, and an antimicrobial agent such as Germaben II from ISP, Inc. The antimicrobial agent serves as a preservative to kill bacteria and fungus that may be introduced into the product during consumer use.

It should be noted that each of the coloring system components in table 1 is provided as a solution having a concentration of that component of the weight percent indicated. For example, D&C Violet #2 is provided as a 1% solution of D&C Violet #2 in mineral oil. Therefore, a sunless tanning formulation comprising 0.4 wt. % concentration of the D&C Violet #2 solution would actually comprise 0.004 wt. % D&C Violet #2. A similar calculation is required to determine the absolute weight percent of each of the coloring system components in the invented formulation.

Optionally, the invented formulation contains a volatile emulient in place of diisodecyl adipate and dimethicone in the solvent system to provide a quick drying formulation. The volatile emulient evaporates quickly from the skin thus providing a formulation that dries at an accelerated rate. The volatile emulient is preferably isododecane, preferably Permethyl 99A from Presperse, Inc., and is present in the invented formulation at a concentration of 0.5–20, preferably 1–15, preferably 1.5–10, preferably 2–5, preferably about 2.5, wt. %. Isododecane can be substituted for diisodecyl adipate and dimethicone in any of the four preferred color variants of the invented formulation as embodied in table 1 (honey, light brown, brown, and dark brown) to provide a quick drying equivalent. A quick drying formulation according to the present invention dries preferably in less than 180, preferably 120, preferably 100, preferably 80, preferably 60, preferably 45, preferably 30, seconds following application to the skin. The formulation is considered "dry" when it no longer feels slippery or wet on the skin.

The unique combination of oil-and water-soluble color components provides a formulation that instantly camouflages the effects of vitiligo upon application to the skin, while the DHA undergoes a chemical reaction with the epidermis to provide a more long-lasting effect even after the skin has been thoroughly cleansed. The water-soluble color components (makeups) present in the inner water phase of the emulsion instantly color the skin upon application. The oil-soluble color components present in the outer silicone phase of the emulsion, in combination with the chemical effects of DHA, provide a more balanced long-term camouflage of vitiligo splotches that is color-matched to the patient's individual skin tone.

The invented formulation is also effective as a self tanning preparation or self tanner. When used as a self tanner, the user applies a quantity of the formulation to the skin in a conventional manner where a tanning effect is desired. Similarly as above, the coloring or make-up components provide an immediate darkening or coloring effect giving the appearance of tanned skin. In the meantime, the DHA reacts with the underlying epidermis to yield a lasting tanned appearance once the make-up components have been washed away. In this manner, a more balanced long-term and color-matched tanning effect is provided.

As indicated above, the invented formulation is in the form of a unique water in oil emulsion, with the water phase being the inner phase and the oil phase (silicone phase) being the outer phase. This water-in-oil system is uncommon in existing sunless tanning creams because DHA solubilizes in the water phase, and therefore water is most commonly the external phase in order to facilitate rapid DHA absorption into the skin. However, a major disadvantage to existing oil-in-water emulsions is that DHA experiences significant atmospheric degradation upon contact with oxygen present in ambient air. Such atmospheric degradation significantly depletes the efficacy of existing sunless tanning creams. However, the water-in-oil emulsion system of the present invention provides a more stable environment for the DHA because atmospheric oxygen does not easily penetrate the outer oil phase to transcend the oil-water phase boundary and attack the DHA within the inner water phase. Though DHA present in an inner water phase will be absorbed, and therefore react to tan the skin, more slowly, a delayed DHA reaction is inconsequential because the makeup color components in the invented formulation provide an instantaneous color effect. Specifically, the makeup components yield the appearance of a color effect while the DHA reaction takes place in the epidermis beneath to provide a lasting color effect.

A second disadvantage of oil-in-water emulsions of present tanning creams is that the external water phase contains water-soluble color components that are easily washed away or distorted from sweat, humidity, splashing, and the like. Such a sunless tanning cream comprising DHA thus could be effectively washed off before the DHA has even absorbed into the skin. The water-in-oil emulsion system of the present invention solves this problem by providing an external oil phase that is hydrophobic. A hydrophobic external phase results in a formulation that is much more resistant to washing away from sweat, humidity, or otherwise upon contact with water before the DHA has been absorbed into the skin. A sunless tanning formulation according to the present invention, applied in a conventional manner, will provide effective camouflage of vitiligo splotches or the appearance of tanned skin for at least 24, preferably 36, preferably 48, preferably 60, 72, 84, 96, or 108, hours.

With reference to table 1, the invented formulation is preferably prepared as follows. First, the components of phase A are combined and mixed together while heating to 75° C. Next, the components of phase B are combined, mixed together, and separately heated to 50° C. Third, the components of phase C are added to the phase B mixture and mixed together to form a heterogeneous mixture of substantially uniform composition at 50° C. The combined phase B/C mixture is added to the phase A mixture with vigorous agitation at 75° C., with the resulting mixture vigorously agitated until a sunless tanning formulation having a substantially uniform composition of all components is formed. The sunless tanning formulation is allowed to cool, and is then packaged for use. The invented formulation is applied to the skin in a conventional manner.

Further aspects of the invention will be understood in conjunction with the following example.

EXAMPLE 1

Various shades of sunless tanning formulations according to the invention were tested in a study with 40 patients as test subjects. The patients were split up into four test groups, each group comprising 10 patients. The patients of each test group were instructed to apply a particular shade of the invented formulation twice daily for 2–3 days, and then as needed to effect adequate camouflage of depigmented splotches caused by vitiligo. Each patient was periodically examined for adverse effects, and product efficacy was investigated respecting four principal concerns: color match, product streaking, cosmetic acceptance, and safety.

Over three years, a multitude of sunless tanning formulations comprising various combinations and concentrations of coloring system components were tested. It was found that the final four shades as described above and delineated in table 1 provided excellent camouflage of vitiligo in all patients tested. The four color shades (honey, light brown, brown and dark brown) formulated as shown in table 1 provided the most effective color match to patient skin tone for the largest number of patients. It was also found that the invented formulation functioned quite well as a sunless tanning cream, producing a long-lasting effective tan without streaking when applied to normal skin. The resulting tan lasted for between 2–5 days in each patient tested with no reapplication of the formulation. Surprisingly and unexpectedly, none of the patients tested reported significant adverse effects such as itching, burning, stinging, erythema, edema, or any other adverse side-effects associated with use of the invented formulation. The absence of any adverse side- effects in even a single patient was a surprising and unexpected result.

Although the hereinabove described embodiments of the invention constitute the preferred embodiments, it should be understood that modifications can be made thereto without departing from the scope of the invention as set forth in the appended claims.

What is claimed is:

1. A sunless tanning formulation comprising a non-makeup cosmetic and a coloring system comprising a water-soluble makeup and an oil-soluble makeup, said non-makeup cosmetic being effective to darken the epidermis via a chemical reaction, said formulation being a water-in-oil emulsion having an inner water phase and an outer oil phase, said water-soluble makeup being present in said inner water phase and said oil-soluble makeup being present in said outer oil phase.

2. A formulation according to claim 1, said formulation being effective to camouflage depigmented splotches on a person's skin immediately upon: application of said formulation to said skin and continuing for at least 24 hours without reapplication of said formulation.

3. A formulation according to claim 1, said formulation being effective to provide the appearance of tanned skin immediately upon application of said formulation to said skin and continuing for at least 24 hours without reapplication of said formulation.

4. A formulation according to claim 1, said formulation further comprising a solvent system and an emulsifying system.

5. A formulation according to claim 1, said non-makeup cosmetic comprising dihydroxyacetone.

6. A formulation according to claim 5, said formulation comprising 1–10 wt. % dihydroxyacetone.

7. A formulation according to claim 1, said water-soluble makeup comprising a makeup or mixture of makeups selected from the group consisting of D&C coloring agents and FD&C coloring agents.

8. A formulation according to claim 7, said water-soluble makeups comprising D&C Violet #2, D&C Green #6, D&C Red #17, FD&C Red #33, FD&C Yellow #5, and FD&C Blue #1.

9. A formulation according to claim 1, said oil-soluble makeup comprising a makeup or mixture of makeups selected from the group consisting of natural and synthetic pigments, fruit and vegetable extracts, and plant extracts.

10. A formulation according to claim 1, said coloring system further comprising melanin.

11. A formulation according to claim 1, said coloring system comprising 0.0001–0.05 wt. % D&C Violet #2, 0.0001–0.05 wt. % D&C Green #6, 0.0001–0.05 wt. % D&C Red #17, 0.0001–0.8 wt. % melanin, 0.01–15 wt. % indigofera tintoria root extract with propylene glycol, 0.01–15 wt. % junglens regia extract, 0.0001–0.15 wt. % FD&C Red #33, 0.0001–0.15 wt. % FD&C Yellow #5, and 0.00001–0.015 wt. % FD&C Blue #1.

12. A formulation according to claim 4, said solvent system comprising a silicone-based solvent, said oil phase comprising a silicone phase formed from said silicone-based solvent.

13. A formulation according to claim 12, said solvent system further comprising an emollient ester.

14. A formulation according to claim 13, said emollient ester being selected from the group consisting of diisodecyl adipate, isopropyl myristate and decyl oleate.

15. A formulation according to claim 12, said silicone-based solvent comprising cyclopentasiloxane with dimethicone copolyol, cyclometicone, and dimethicone.

16. A formulation according to claim 4, said emulsifying system comprising dimethicone copolyol beeswax, PEG-30 dipolyhydroxystearate, sorbitan isostearate, and decyl glucoside.

17. A formulation according to claim 1, further comprising an effective amount of an antimicrobial agent.

18. A formulation according to claim 4, said formulation further comprising 0.5–20 wt. % isododecane.

19. A formulation according to claim 18, wherein said formulation dries in less than 180 seconds upon application to skin.

20. A sunless tanning formulation effective to camouflage the effects of vitiligo when applied to skin, said formulation being a water-in-oil emulsion having an inner water phase and an outer oil phase, said formulation comprising an effective amount of dihydroxyacetone, a coloring system comprising an oil-soluble makeup present in said outer oil phase and a water-soluble makeup present in said inner water phase, an emulsifying system effective to provide said water-in-oil emulsion, and a solvent system comprising a silicone-based solvent.

21. A method of camouflaging the effects of vitiligo comprising the step of applying a formulation to depigmented splotch on a patient's skin, said formulation being a water-in-oil emulsion having an inner water phase and an outer oil phase, said formulation comprising an effective amount of dihydroxyacetone, and a coloring system comprising an oil-soluble makeup present in said outer oil phase and a water-soluble makeup present in said inner water phase.

22. A method of providing the appearance of tanned skin comprising the step of applying a sunless tanning preparation to the skin, said preparation comprising a water-in-oil emulsion having an inner water phase and an outer oil phase, a water-soluble makeup present in said inner water phase, an oil-soluble makeup present in said outer oil phase, and dihydroxyacetone present in said inner water phase, said dihydroxyacetone being thereby shielded from atmospheric oxygen, wherein said water-soluble makeup provides an immediate coloring effect yielding the appearance of tanned skin, said dihydroxyacetone undergoing a chemical reaction with the epidermis of said skin to provide a lasting appearance of tanned skin after said water-soluble makeup has washed away.

23. A method according to claim 22, wherein, in the following order:
   a) said water-soluble makeup provides an instantaneous color effect on the skin upon application of said preparation to the skin; and
   b) said dihydroxyacetone, due to its presence in said inner water phase, is slowly absorbed into the skin resulting in a delayed chemical reaction, relative to the moment of application of said preparation to the skin, between the dihydroxyacetone and the epidermis to darken the epidermis, thereby yielding a lasting tanned appearance to said skin after said water-soluble makeup and said oil-soluble makeup have been washed away.

24. A method according to claim 22, said preparation being resistant to washing away from sweat, humidity or contact with water before said dihydroxyacetone has been absorbed into the skin.

25. A method according to claim 22, said skin retaining a tanned appearance for at least 48 hours following application of said preparation without reapplication thereof.

26. A sunless tanning cream comprising melanin indigofera tintoria root extract, junglens regia extract and dihydroxyacetone.

27. A sunless tanning cream according to claim 26, comprising 0.0001–0.8 wt. % melanin, 0.01–15 wt. % indigofera tintoria root extract, 0.01–15 wt. % junglens regia extract.

28. A sunless tanning cream according to claim 26, comprising 1–10 wt. % dihydroxyacetone.

29. A sunless tanning cream according to claim 26, comprising 0.001 wt. % melanin, 0.5 wt. % indigofera tintoria root extract, and 2 wt. % junglens regia extract.

30. A sunless tanning cream according to claim 29, comprising 2 wt. % dihydroxyacetone.

31. A sunless tanning cream according to claim 26, comprising 0.012 wt. % melanin, 0.5 wt. % indigofera tintoria root extract, and 1.99 wt. % junglens regia extract.

32. A sunless tanning cream according to claim 31, comprising 4.04 wt. % dihydroxyacetone.

33. A sunless tanning cream according to claim 26, comprising 0.1 wt. % melanin, 0.5 wt. % indigofera tintoria root extract, and 1.5 wt. % junglens regia extract.

34. A sunless tanning cream according to claim 33, comprising 6 wt. % dihydroxyacetone.

35. A sunless tanning cream according to claim 26, comprising 0.5 wt. % melanin, 1 wt. % indigofera tintoria root extract, and 3 wt. % junglens regia extract.

36. A sunless tanning cream according to claim 35, comprising 7 wt. % dihydroxyacetone.

* * * * *

UNITED STATES PATENT AND TRADEMARK OFFICE
CERTIFICATE OF CORRECTION

PATENT NO. : 6,630,130 B1
DATED : October 7, 2003
INVENTOR(S) : Pearl Grimes et al.

It is certified that error appears in the above-identified patent and that said Letters Patent is hereby corrected as shown below:

Column 7,
Line 56, please delete ":" (colon).

Signed and Sealed this

Third Day of February, 2004

JON W. DUDAS
*Acting Director of the United States Patent and Trademark Office*